United States Patent [19]

Goldstein

[11] Patent Number: 4,635,636

[45] Date of Patent: Jan. 13, 1987

[54] MICROSPIKE SURGICAL APPROXIMATOR

[75] Inventor: Marc Goldstein, New York, N.Y.

[73] Assignee: Cornell Research Foundation, Inc., Ithaca, N.Y.

[21] Appl. No.: 746,166

[22] Filed: Jun. 18, 1985

[51] Int. Cl.$^4$ ............................................. A61B 17/12
[52] U.S. Cl. ................................. 128/334 R; 128/346; 128/334 C; 269/45; 24/507
[58] Field of Search ............... 128/334 R, 346, 303 R, 128/334 C, 337, 92 E, 92 EA, 335; 24/457, 458, 459, 531; 269/43, 45, 152

[56]  References Cited

U.S. PATENT DOCUMENTS

| | | | |
|---|---|---|---|
| 2,631,585 | 3/1953 | Siebrant | 128/92 EA |
| 3,035,582 | 5/1962 | Seiger | 128/321 |
| 3,467,079 | 9/1969 | James | 128/303 R |
| 3,561,448 | 2/1971 | Peternel | 128/334 |
| 3,746,002 | 7/1973 | Haller | 128/322 |
| 3,802,437 | 4/1974 | Kees, Jr. | 128/325 |
| 4,146,022 | 3/1979 | Johnson et al. | 128/92 EA |
| 4,165,747 | 8/1979 | Bermant | 128/334 |
| 4,200,107 | 4/1980 | Reid | 128/335 |
| 4,245,638 | 1/1981 | Lebeck et al. | 128/334 |
| 4,316,470 | 2/1982 | Braun et al. | 128/346 |
| 4,324,248 | 4/1982 | Perlin | 128/325 |
| 4,331,150 | 5/1982 | Braun et al. | 128/334 |
| 4,331,150 | 5/1982 | Braun et al. | 128/334 C |
| 4,337,774 | 7/1982 | Perlin | 128/325 |
| 4,424,811 | 1/1984 | Groot | 128/435 |
| 4,506,669 | 3/1985 | Blake, III | 128/334 |

OTHER PUBLICATIONS

Microsurgical Composite Tissue Transplantation.
L. V. Wagenknecht, MD, H. Klosterhalfen, MD, & C. Schirren, MD, "Microsurgery in Andrologic Urology I. Refertilization", Mar./Apr. 1980, pp. 373-376, Journal of Microsurgery.
David J. Albert & Frank C. Ott, Jr., "A Simple Stabilizing Clamp for Microscopic Vasovasostomy", Jul., The Journal of Urology, vol. 120, pp. 77-79.
Fray F. Marshall, MD, "Microsurgical Vasovasostomy Clamp", Apr. 1979, p. 419, Urology, vol. XIII, No. 4.
Arnold M. Belker, MD, "Technical Aids for Vasovasostomy", Dec. 1982, pp. 635-637, Urology, vol. XX, No. 6.
Stanwood S. Schmidt, MD, "A Simple Vas Approximator", Jun. 1983, pp. 630-631, Urology, Vol. XXI, No. 6.

Primary Examiner—Richard C. Pinkham
Assistant Examiner—Gary Jackson
Attorney, Agent, or Firm—Jones, Tullar & Cooper

[57] ABSTRACT

A microspike surgical approximator usable to stabilize the ends of ducts or vessels being anastomosed microsurgically includes a pair of approximating clamps slidable along a bar which is foldable at a point intermediate the approximating clamps. Each clamp includes a stationary blade which is alidable along the bar and a pivoted blade that is movable with respect to the stationary blade. The major faces of the blades terminate in lower duct or vessel clamping portions, each of which has a curved jaw segment. These jaw segments cooperate to form an annular duct or vessel receiving aperture. A plurality of microspikes are secured to the curved jaw segments and extend into the duct or vessel receiving aperture. During vessel stabilization, the microspikes contact the adventitia of the vessel to hold the duct or vessel ends with minimal trauma.

1 Claim, 2 Drawing Figures

MICROSPIKE SURGICAL APPROXIMATOR

FIELD OF THE INVENTION

The present invention is directed generally to a surgical approximator. More particularly, the present invention is directed to a surgical approximator having improved duct or vessel stabilization characteristics. Most specifically, the present invention is directed to a surgical approximator having microspikes which engage and hold the ends of the duct or vessel during anastomosis. The microspikes are formed of stainless steel wire or the like and extend inwardly into the annular duct or vessel receiving area of the surgical approximator's curved clamping jaw segments. In a microsurgical procedure such as a vasovasostomy, the microspike surgical approximator securely stabilizes the two ends of the vas deferens during anastomosis. The microspikes contact only the adventitia of the duct or vessel being anastomosed and do not penetrate the endothelium or mucosa. Since vessel stability is achieved by engagement with the microspikes, high clamping forces are not required so there is little likelihood of trauma to the duct or vessel.

DESCRIPTION OF THE PRIOR ART

During surgical procedures and particularly during microsurgical procedures involving the re-joining by anastomosis of previously severed ducts or vessels such as the vas deferens or a fallopian tube, proper stabilization of both ends of the duct or vessel is extremely important. Slippage of one or the other ends of the duct or vessel may necessitate an enlargement of the incision to locate the lost end of the duct or vessel or may cause damage to the end of the duct or vessel should one or more sutures be pulled out.

A number of microsurgical aproximators are generally known in the art. These typically are comprised of two microclips attached to a metal bar and slidable along the bar to vary the spacing between the two microclips. Slippage of the ends of the duct or vessel held in apposition to each other by such surgical approximators is a problem that has vexed microsurgeons since the start of the specialty. Various attempts have been made to solve this problem but these have not proved particularly successful.

One means of preventing slippage of an article held in a clamp is to provide the clamp with sufficient clamping pressure that there is no possibility of slippage. Another proposed solution for use with surgical approximating clamps has been the provision of some type of surface etching or roughening applied to the interior blade surfaces of the clamps. In yet another proposal, the inner clamping surfaces of the approximating blades have been provided with a friction increasing surface such as a foam rubber material or the like.

Damage to the mucosa or endothelium due to the employment of microsurgical clips or approximators is directly related to the closing pressure of the clip and to the length of time that the clip is employed. Previous attempts to prevent or minimize slippage of the vessels during anastomosis, which can be a very harmful occurrence particularly during a delicate microsurgical procedure, have utilized clips or approximators having very high closing pressures. As was indicated above, these high clip closing pressures have increased the incidence and severity of endothelial or mucosal damage. Thus high closing pressure microsurgical approximators have failed to render a satisfactory solution to the problem.

Provision of an etched, cross hatched or otherwise roughened clamp blade or clip inner surface has also not proved satisfactory. The abdominal end of the vas deferens is particularly prone to slippage out of the clamp at the most critical point in the anastomosis. The use of roughened clamp blade faces has not, by itself, been sufficient to prevent this slippage or duct or vessel movement. High clamping pressures remain needed with their previously discussed trauma to the mucosa and endothelium.

In a further attept to minimize duct or vessel slippage during microsurgical procedures, some surgeons have glued or otherwise attached pieces of foam rubber or rubber tubing to the ends of the clamps. While this modification has reduced duct or vessel slippage to some degree, the foam or other friction increasing attachments cannot be autoclaved and is not long lasting. The surgeon must therefore attach new, sterile foam or rubber pieces to the surgical approximator's clamping blades prior to each procedure. As can readily be understood, such a solution is not practical on a continuing basis.

As can be appreciated from the above discussion, there is a need for a surgical approximator, particularly one usable in microsurgical procedures, which securely holds the two ends of the duct or vessel in stable apposition with no possibility of slippage. The microspike surgical approximator in accordance with the present invention provides such a capability while not damaging the duct or vessel itself.

SUMMARY OF THE INVENTION

It is an object of the present invention to provide a surgical approximator.

Another object of the present invention is to provide a surgical approximator particularly usable in microsurgical procedures.

A further object of the present invention is to provide a surgical approximator which facilitates surgical anastomoses.

Still another object of the present invention is to provide a surgical approximator which holds the two ends of a duct or vessel in stable apposition during anastomosis.

Yet a further object of the present invention is to provide a surgical approximator which utilizes microspikes.

Still yet another object of the present invention is to provide a microspike surgical approximator that does not rely on high clamping pressures.

Even yet a further object of the present invention is to provide a microspike surgical approximator that is durable and can be autoclaved.

As will be discussed in greater detail in the description of the preferred embodiment as is set forth subsequently, the microspike surgical approximator in accordance with the present invention employs microspikes which protrude inwardly from the inner surface of the approximating blades. These protrusions never penetrate the mucosa or endothelium of the vessel being approximated. In a typical microspike surgical approximator, in accordance with the present invention, fine stainless steel wire having a diameter of 50 to 150 microns and a length of 250 to 300 microns is used to form the microspikes. These microspikes are permanently secured to the blades of the approximator's curved jaw segments and extend into the annular vessel receiving aperture defined by the two jaws. Only the adventitia is grasped by the microspikes so that duct or vessel stability is obtained without damage to the endothelium or mucosa of the vessel or penetration of the lumen of the duct or vessel.

The microspike surgical approximator, in accordance with the present invention, does not rely on clamping pressure to secure the ends of the duct or vessel in place. Since high clamping pressures are not required, there is no incidence of pressure related vessel damage. Accordingly, the duct or vessel being anastomosed is not harmed by application of the microspike surgical approximator of the present invention to it.

The fine stainless steel clamp protrusions or spikes form a secure, positive duct or vessel stabilizing assembly. They do not rely on increased friction to provide holding capacity as was the case with the prior clamps that required a roughened clamp surface. Again, high clamp pressure is not needed as is the situation with roughened prior clamp surfaces. This further minimizes duct or vessel damage.

The microspikes formed on the clamping blade's inner curved jaw surfaces are preferably made of stainless steel wire. This renders the microspike surgical approximator inert and autoclavable. In contrast with prior art structures that use foam pads and other porous and resilient friction increasing approaches, the microspike surgical approximator in accordance with the present invention is reusable after autoclaving and does not require a new application of foam padding prior to each use. Even if the foam material applied to approximator blades in accordance with the prior art is autoclavable, it is apt to lose its resiliency. The microspike surgical approximator in contrast is made of stainless steel or other similar material so that it is non porous, completely inert and readily autoclavable.

The microspike surgical approximator, in accordance with the present invention, provides a very satisfactory assembly which holds two ends of a duct or vessel in stable apposition during anastomosis. Low clamping pressures are sufficient to hold the duct or vessel ends in the approximator so damage to the mucosa and endothelium of the duct or vessel are prevented. Ease of autoclaving and simplicity and durability are also afforded by the microspike surgical approximator in accordance with the present invention.

BRIEF DESCRIPTION OF THE DRAWINGS

While the novel features of the microspike surgical approximator, in accordance with the present invention, are set forth with particularity in the appended claims, a full and complete understanding of the invention may be had by referring to the detailed description of the preferred embodiment as set forth hereinafter and as may be seen in the accompanying drawings in which:

DESCRIPTION OF THE PREFERRED EMBODIMENT

Figure 1:
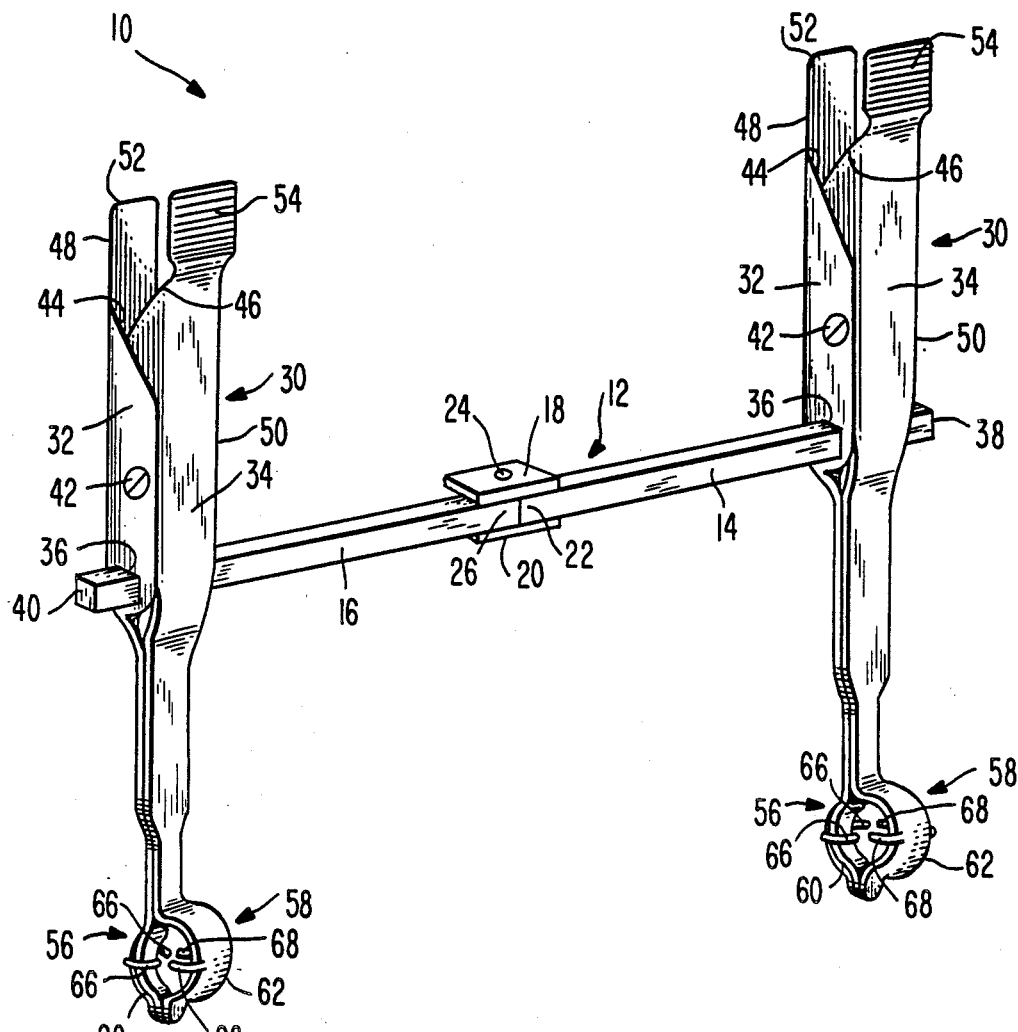
FIG. 1 is a perspective view of the microspike surgical approximator in accordance with the present invention; and, FIG. 2 is a perspective view of the duct or vessel receiving portion of one of the approximating clamps.

Referring initially to FIG. 1, there may be seen, generally at 10, a microspike surgical approximator in accordance with the present invention. The microspike surgical approximator 10 is specifically intended to hold end portions of a previously separated duct or vessel in apposition so that they can be surgically reconnected, typically by suturing. In one of its primary intended applications, the microspike surgical approximator 10 is utilized to join previously severed ends of the human vas deferens in a surgical technique referred to as a vasovasostomy. Other typical applications are in stabilizing the previously severed ends of a fallopian tube or a blood vessel. Such vessels typically have a central hollow passage or lumen surrounded by various tissue layers. The structure of such ducts or vessels is well known to those familiar with surgical techniques and need not be discussed in detail.

Microspike surgical approximator 10 in accordance with the present invention can be characterized as a folding bar, sliding clamp approximator. A generally rectangular, elongated bar, generally at 12, is divided into a fixed bar segment 14 and a folding bar segment 16. Spaced upper and lower hinge plates 18 and 20, respectively, are secured to the inner end 22 of fixed bar segment 14 by suitable means such as welding, and receive a pivot pin 24 which passes through an inner end 26 of folding bar segment 16. This structure is exemplary of a number of possible assemblies which can be used to render folding bar 12 capable of being folded intermediate its ends.

A pair of generally identical approximating clamps 30 are slidably carried on folding bar 12 with one clamp being positioned on each of the fixed and folding segments 14 and 16, respectively. Each approximating clamp 30 is comprised of a stationary blade 32 and a pivoted blade 34. Stationary blade 32 includes a generally rectangular aperture 36 which is sized to receive the free ends 38, 40 of fixed and folding bar segments 14 and 16, respectively. In this way each approximating clamp is slidable along its bar segment 14 or 16. The pivoted blade 34 is attached to the stationary blade 32 of clamp 30 by use of a screw 42 that passes through aligned apertures in side faces 44 and 46 of stationary blade and pivoted blade 32 and 34, respectively. A suitable spring (not shown) is positioned between the stationary and pivoted blades 32 and 34, and holds them in the closed position, as seen in FIG. 1.

The major or front faces 48, 50 of stationary and pivoted blades 32, 34, respectively, are provided, at first, upper ends, with actuating portions 52, 54. In use, the surgeon applies finger pressure to these actuating portions 52 and 54 to move pivoted blade 34 with respect to stationary blade 32 against the low closing pressure, in the range of 15 grams or less, exerted by the spring (not shown). Such finger pressure opens the lower, vessel engaging clamping portions 56, 58 of blades 32, 34 by moving lower movable clamping portion 58 with respect to lower fixed clamping portion 56.

Figure 2:
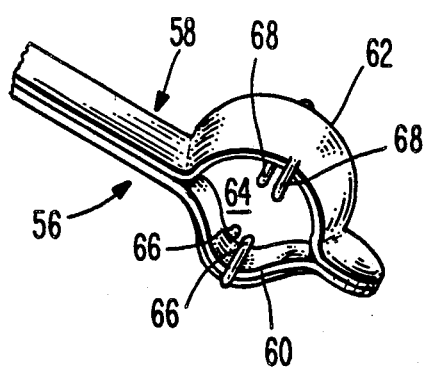

Each lower clamping portion 56 and 58 of fixed and pivoted blade segments 32 and 34, respectively, of each approximating clamp 30 terminates in a generally curved jaw segment 60, 62. As may be seen most clearly in FIG. 2, the curved jaw segments 60 and 62 of the stationary and pivoted blades 32 and 34 of each clamp 30 form a generally annular duct or vessel receiving aperture 64. A plurality of microspikes 66 are provided on stationary blade jaw 60 and a plurality of complimentary microspikes 68 are provided on pivoted blade jaw 62. Each microspike 66, 68 extends into vessel or duct receiving aperture 64 and has a diameter and length sized in accordance with the diameter of the duct or vessel to be held in the vessel receiving aperture 64 by the stationary and pivoted jaw segments 60 and 62 of each approximating clamp 30. The microspikes 66 on stationary jaw 60 and the microspikes 68 on pivoted jaw 62 are spaced generally opposite each other with there being two microspikes on each jaw. As seen most clearly in FIG. 2, the microspikes on each jaw segment are located on either side of the jaw segment with the two microspikes on each jaw being generally parallel to each other.

Each microspike 66, 68 is, in the preferred embodiment, formed from stainless steel wire that is attached to the jaw segment by soldering or the like. Alternatively, the microspikes 66, 68 could be formed integrally with the clamping jaw segments 60, 62 during manufacture of the approximating clamp 30. When the microspike surgical approximator 10 is to be used in holding the ends of a human vas deferens during anastomosis thereof, each microspike 66, 68 has a diameter of generally about 50 to 150 microns and a length of generally about 250 to 300 microns. For blood vessel usage, smaller microspikes are used and if the vessel is larger, than larger microspikes are used. These spikes are positioned in the duct or vessel receiving aperture 64, and the aperture itself is so sized that the microspikes 66, 68 never penetrate the mucosa or endothelium of the structure being approximated. Instead, the microspikes penetrate only the adventitia of the duct or vessel. It will, of course, be understood that a surgical approximator 10 is suitable for use with ducts or vessels of a certain size range and that various approximators 10 will be needed to encompass the range of duct or vessel sizes encountered during various microsurgical techniques. These various microspike surgical approximators will utilize approximating clamps 30 having various sizes of duct or vessel receiving apertures 64 and various lengths and diameters of microspikes 66, 68. In all instances, the placement and size of the microspikes will be such that only the adventitia of the stabilized duct or vessel will be engaged by the microspikes.

In accordance with the preferred embodiment of the microspike surgical approximator, each curved jaw segment 60 and 62 of each approximating clamp 30 utilizes two inwardly directed microspikes 66 and 68, respectively. This could be varied, if necessary. However, in numerous microsurgical reconstructions of the human vas deferens, the microspike surgical approximator 10, in accordance with the present invention, has proven extremely useful and achieves superb duct or vessel stability with minimal trauma. The elongated folding bar 12 can be folded in either direction so that the vas or vessel lumen can be exposed equally well during both anterior and posterior wall anastomoses. The folding bar 12 may be stabilized with a small locking needleholder.

While a preferred embodiment of a microspike surgical approximator, in accordance with the present invention, has been set forth fully and completely hereinabove, it will be obvious to one of skill in the art that a number of changes in, for example, the materials used for the clamps, the clamp pivot assembly, the spring biasing means and the like could be made without departing from the true spirit and scope of the present invention which is to be limited only the following claims.

What is claimed:

1. A microspike surgical approximator usable to stabilize ends of a duct or vessel during microsurgical anastomosis of the duct or vessel, said microspike surgical approximator comprising:

a generally rectangular elongated bar foldable intermediate its ends and having a fixed bar segment and a folding bar segment joined together by spaced hinge plates secured to said fixed bar segment and a pivot pin passing through said hinge plates and said folding bar segment;

at least first and second approximating clamps slidably positioned on said bar with one of said clamps being slidably positioned on each of said fixed and folding bar segments, respectively;

each said approximator clamp having a stationary blade which includes a generally rectangular aperture sized to receive one of said fixed and folding bar segments so that said stationary blade is slidably attached to said bar, and a pivoted blade pivotably attached to said stationary blade, said stationary blade and said pivoted blade of each said approximating clamp being spring biased;

actuating means at first ends of said stationary and pivoted blades of each said approximating clamp, said actuating means being engageable by a user of said approximator to pivot said pivotable blade with respect to said stationary blade;

duct or vessel clamping portions at second ends of said stationary and pivoted blades of each said approximating clamp, said duct or vessel clamping portions including curved jaw segments on each said stationary and pivoted blades, said curved jaw segments cooperating to form an annular duct or vessel receiving aperture; and a plurality of spaced microspikes on said curved jaw segments of each of said stationary and pivoted blades, said microspikes on said stationary blade being opposite to said microspikes on said pivoted blade, each of said microspikes extending inwardly into said annular duct or vessel receiving aperture, said microspikes being formed on stainless steel with each said microspike having a diameter and a length sized to penetrate only the adventitia of the duct or vessel during microsurgical anostomosis of the duct or vessel with no penetration of the mucosa or endothelium of the duct or vessel.

* * * * *